United States Patent [19]

Resnick et al.

[11] Patent Number: 5,352,581
[45] Date of Patent: Oct. 4, 1994

[54] SENSITIVE YEAST GENETIC SYSTEM FOR IDENTIFYING AGENTS CAUSING DOUBLE-STRANDED DNA DAMAGE

[75] Inventors: Michael A. Resnick, Chapel Hill, N.C.; Torston Nilsson-Tillgren, Copenhagen, Denmark

[73] Assignee: United States/National Institutes of Health, Rockville, Md.

[21] Appl. No.: 897,577

[22] Filed: Jun. 11, 1992

Related U.S. Application Data

[63] Continuation of Ser. No. 328,168, Mar. 24, 1989, abandoned.

[51] Int. Cl.$^5$ .............................................. C12Q 1/68
[52] U.S. Cl. ..................................... 435/6; 435/255.1; 435/255.2; 435/941; 435/942
[58] Field of Search ................... 435/6, 7.31, 255, 256, 435/255.2, 255.1

[56] References Cited

OTHER PUBLICATIONS

Mortimer, et al., "Mitotic Chromosome Loss in a Radiation-Sensitive Strain of Yeast *Saccharomyces cerevisiae*," Proc. Natl. Acad. Sci, Sep. 1981, vol. 78, pp. 5778–5782.
Goodenaugh Genetics (1974) Holt, Rinehart & Winston, Inc. New York, N.Y. p.p. 139–179.
Webster's II New Riverside University Dictionary p. 589.
Holmberg, Carlsberg Res. Commun 47 233–44 (1982).
Resnick et al Mutation Research 167: 47–60 (1986).
Rose et al. *The Yeasts VI* Academic Press, New York, N.Y. (1969) p. 403–416.
Mortimer et al *The Yeasts VI* Academic Press New York, N.Y. (1969) p. 393–395.
Nillson-Tillgren et al Carlsberg Res. Commun 46 (1-2) 1981 65–76.
Resnick et al Proc Natl Acad Sci 86 Apr. 1989 2276–2280.
Whittaker et al Mol Gen Genet 215: 10–18 (1988).
Hartwell, L. H. & Smith, D. (1985) *Genetics*, 110, 381–395. "Altered Fidelity of Mitotic Chromosome Transmission in Cell Cycle Mutants of *S. cerevisiae*".
Waldren, C. Correll, L. Sognier, M. A. & Puck, T. T. (1986), *Proc. Natl. Acad. Sci. USA*, 83, 4839–4843 "Measurement of low levels of X-ray mutagenesis in relation to human disease".
Liras, P. McCuker, J. Mascioll, S. & Haber, I. E. (1978), *Genetics*, 88, 651–671, "Characterization of a Mutation in Yesat Causing Nonrandom Chromosome Loss During Mitosis".
Tolstoryukow, I. I., Efremov, B. D. & Bliznik, K. M. (1983), *Genetika*, 19, 897–902 Russian "Identification of Linkage Groups Using Induced Mitotic Haploidization".
Chow, T. Y. K., & Resnick, M. A. (1987) *J. Biol chem.* 262, 17659–17667. "Purification and Characterization of an Endo-Exonuclease from *Saccharomyces cerevisiae* That is Influenced by the RAD52 Gene".
DiNardo, S. Voelkel, K. & Sternglanz, R. (1984), *Proc. Natl. Acad. Sci. USA*, 81, 2616–2620 "DNA topoisomerase II mutant of *Saccharomyces cerevisiae*: Topoisomerase II is required for segregation of daughter molecules at the termination of DNA replication".
Schatz, P. J., Solomon, F. & Botstein, D. (1986), *Mol. Cell. Biol.* 6, 3722–3733. "Genetically Essential and (List continued on next page.)

*Primary Examiner*—Margaret Parr
*Assistant Examiner*—S. Houtteman
*Attorney, Agent, or Firm*—Knobbe, Martens, Olson & Bear

[57] ABSTRACT

A sensitive, yeast-based genetic system for identifying agents causing double-strand DNA damage is described. The system comprises a yeast strain containing either chromosomes having divergent (homeologous) DNA sequences, a single nonhomologous chromosome or a single artificial chromosome with suitable genetic markers so that double-strand damage leading to the loss of such chromosome due to the inability to undergo recombinational repair with a homolog is detected.

4 Claims, 4 Drawing Sheets

OTHER PUBLICATIONS

Nonessential-Tubulin Genes Specify Functionally Interchangeable Proteins".

Resnick, M. A., Zimmermann, F. K., Fogel, S. & Bloom, K. (1989) *Mutat. Res.*, in press. pp. 35–45; "The Genetic Detection, Mechanism, and Relevance of Chemically Induced Chromosome Aneuploidy in Yeast".

Resnick, M. A. (1976), *J. Thero. Biol*, 59, 97–106. "The Repair of Double-Stranded Breaks in DNA: A Model Involving Recombination".

Resnick, M. A. & Martin, P. (1976) *Mol. Gen. Genet.*, 143, 119–129. "The Repair of Double-Stranded Breaks in the Nuclear DNA of *Saccharomyces cerevisiae* and Its Genetic Control".

Holmberg, S., (1982) *Carlsberg Res. Commun.* 47, 233–244. "Genetic Differences Between *Saccharomyces carlsbergensis* and *S. cerevisiae* II Restriction Endonuclease Analysis of Genes in Chromosome III".

Resnick, M. A., Stasiewicz, S. & Game, J. C. (1983) *Genetics*, 104, 583–602. "Meiotic DNA Metabolism in Wild-Type and Excision-Deficient Yeast Following UV Exposure".

Carle, G. F. & Olson, M. V. (1985), *Proc. Nat'l. Acad. Sci. USA*, 82, 3756–3760. "An Electrophoretic Karyotype for Yeast".

Mortimer, R. K. & Schild, D. (1985) *Microbiol. Rev.*, 49, 181–212. "Genetic Map of *Saccharomyces cerevisiae*, Edition 9".

Newlon, C. S., Green, R. P., Hardeman, K. J., Kim, K. E., Lipchitz, L. R., Palzkill, T. G., Synn, S. & Woody, S. T. (1986) in Yeast Cell Biology, ed. G. Hicks, J. (Liss, New York), pp. 211–223 "Structure and Organization of Yeast Chromosome III".

Fink, G. R. & Styles, C. A. (1974) *Genetics*, 77, 231–244. "Gene Conversion of Deletions in the HIS4 Region of Yeast".

Peterson, J. G. L., Nilsson-Tillgren, T., Kielland-Brandt, M. C., Gjermansen, C. & Holmberg, S. (1987), *Curr. Genet.*, 12, 167–174, "Structural Heterozygosis at Genes ILV1 and ILV5 in *Saccharomyces carlsbergensis*".

Niisson-Tillgren, T., Gjermansen, C. Holmberg, S., Petersen, J. G. L. & Klelland-Brandt, M. C. (1986) *Carlsberg Res. Commun.*, 51, 309–326. "Analysis of Chromoxome V and the ILV1 Gene From *Saccharomyces carlsbergensis*".

Brunborg, G., Resnick, M. A., & Williamson, D. H. (1980), *Radiat. Res.* 82, 547–588. "Cell-Cycle Specific Repair of DNA Double-Strand Breaks in *Saccharomyces cerevisiae*".

Resnick, M. A. (1979), *Adv. Radiat. Biol.*, 8, 175–217. "The Induction of Molecular and Genetic Recombination in Eukaryotic Cells".

Resnick, M. A., (1979), *Mutat. Res.*, 42, 131–134. "Repaired Double-Straind Breaks in Nuclear DNA are not Always Lethal".

Ho, K. S. Y. & Mortimer, R. K. (1973), *Mutat. Res.*, 20, 45–51. "Induction of Dominant Lethality by X-Rays in a Radiosensitive Strain of Yeast".

Resnick, M. A., Nitiss, J., Edwards, C. & Malone, R. E. (1986), *Genetics*, 113, 531–550. "Meiosis Can Induce Recombination in RAD52 Mutants of *Saccharomyces cerevisiae*".

Chow, T. Y. K., & Resnick, M. A., (1988), *Mol. Gen. Genet.*, 211, 41–48. "An Endo-Exonuclease Activity of Yeast that Requires a Functional RAD52-gene".

Esposito, M. S., Moleas, D. T., Bjornstad, K. A. & Holbrook, L. L., (1986), *Curr. Genet.*, 10, 425–433. "The REC46 gene of *Saccharomyces cerevisiae* controls mitotic chromosomal stability, recombination and sporulation cell-type and life cycle stage-specific expression of rec46-1 mutation".

Kouprina, N. Y., Pachina, O. B., Nikolaishwill, N. T., Tsouladze, A. M. & Larionov, V. L. (1988), *Yeast*, 3, 187–200. "Genetic Control of Chromosome Stability in the Yeast *Saccharomyces cerevisiae*".

Fitzgerald-Hayes, M. (1987) *Yeast*, 3, 187–200. "Yeast Centromeres".

\* III cere.
○ III carl.

SENSITIVE YEAST GENETIC SYSTEM FOR IDENTIFYING AGENTS CAUSING DOUBLE-STRANDED DNA DAMAGE

This application is a continuation of U.S. patent application Ser. No. 328,168, filed Mar. 24, 1990, now abandoned.

The present invention is related generally to the recombinational repair mechanism for maintaining genomic stability. More particularly, the present invention is related to providing a diploid strain of *Saccharomyces cerevlstae* containing at least a single artificial chromosome or a pair of chromosomes having divergent (homoeologous) DNA sequences with suitable genetic markers such that double-strand damage leading to the loss of the chromosome due to the failure to undergo recombinational repair with a homolog is detected, thus allowing the identification of a chemical or physical agent that causes DNA double-strand damage. Such a simple and sensitive, yeast-based genetic system for the detection of DNA double-strand primary or secondary damage was not heretofore available.

SUMMARY OF THE INVENTION

It Is, therefore, an object of the present invention to provide a diploid *S. cerevisiae* strain with genetic markers and a pair of functionally comparable chromosomes having divergent (homoeologous) DNA sequences comparable chromosomes or a diploid with an artificial chromosome but appropriately marked genetically, the resulting chromosomal constitution having the following properties:

(a) enabling the genetic detection of chromosomal loss in mitotic cells arising naturally or as a result of exposure to a chemical or physical agent; and (b) enabling differentiation between DNA double-strand damage and other types of DNA damage.

It is another object of the present invention to provide a method for detecting chemical or physical agent-induced chromosomal changes, comprising the steps of:

(a) exposing the yeast strain of the present invention to an agent whose DNA damaging effect is to be determined;

(b) then plating the strain from step (a) to a suitable selective or diagnostic medium; and (c) thereafter examining plated colonies of step (b) for the loss of a divergent or artificial chromosome.

It is a further object of the present invention to provide a method for identifying DNA double-strand damage leading to aneuploidy.

It is yet another object of the present invention to provide a yeast strain containing a single artificial chromosome with appropriate genetic markers so that double-strand damage will lead to loss of the chromosome due to inability to undergo recombinational repair with a homolog.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description of a diploid *Saccharomyces cerevlstae* strain containing a single pair of divergent chromosomes (chromosome III) when considered in connection with the accompanying drawings—.

DETAILED DESCRIPTION OF THE INVENTION

The above and various other objects and advantages of the present invention are achieved by a diploid *S. cerevisiae* strain in which all the chromosomes are homologous, except for one pair which preferably is composed of a resistance genetic marker-bearing chromosome of *S. cerevisiae* and a functionally equivalent but DNA divergent resistance genetic marker-bearing chromosome from the related yeast *S. carlsbergenisis*, the divergence preventing recombinational interactions whereby DNA double-strand damage leads to the inactivation of one or the other of the divergent chromosomes and consequent loss of genetic markers, thereby allowing selective and sensitive detection of the chromosomal loss.

Figure 4:
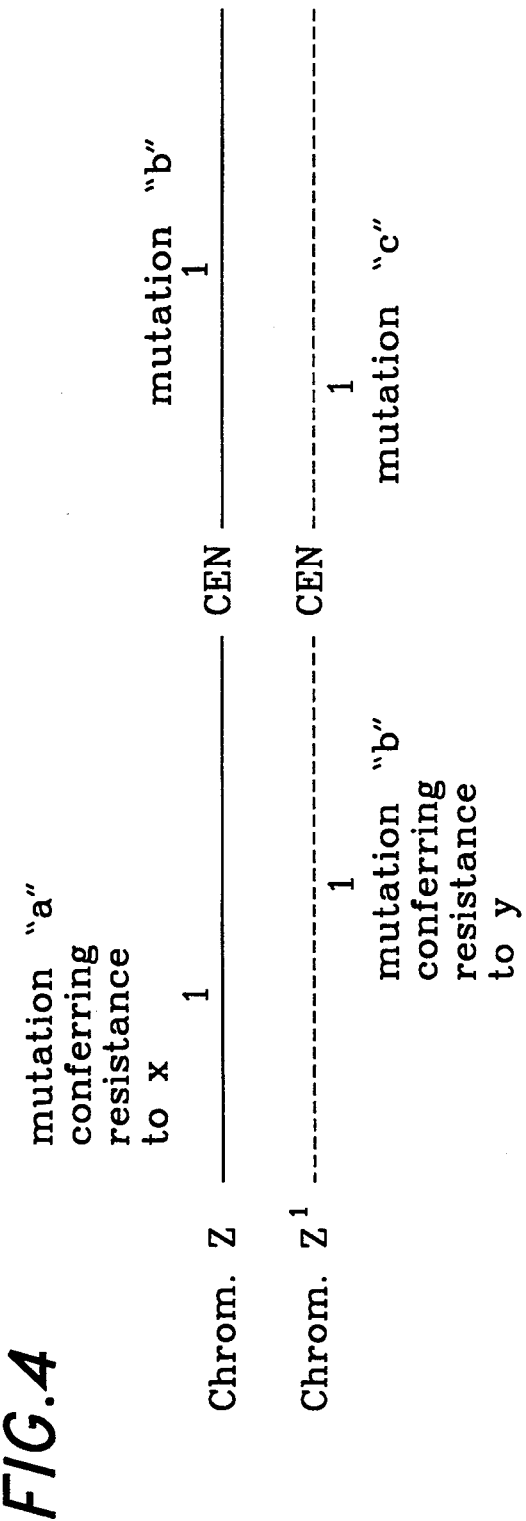
FIG. 4 is an illustration depicting two DNA divergent chromosomes in a yeast strain which can be used to detect double-stranded DNA damage according to the present invention. The illustrated chromosomes contain selectable recessive genetic markers "a", "b", "c", and "d".

The basic features of the present invention are accomplished by developing a yeast strain with divergent chromosomes, e.g., Z and $Z^1$, shown in FIG. 4 containing selectable recessive genetic markers. This is illustrated in FIG. 4.

Stationary G-1 cells are treated with an agent. Cells are plated to medium containing factor x and to medium containing factor y. These factors prevent the growth of wild type yeast. The appearance of the recessive marker "a" or "b" (shown in FIG. 4), such as by mutation or chromosome loss, will enable the expression of resistance to either x or y. Since chromosomal survival, when a chromosome contains double-strand damage (such as double-strand breaks), requires recombination, the inability to repair due to divergence between the chromosomes will result in inactivation of the chromosome containing the damage. As a result, most of the resistant mutants will also express the other recessive marker on the same chromosome for which resistance is detected. Agents which only induce resistance, and not associated expression of linked recessive markers, are considered as single-strand mutagens.

An alternative system based on an artificial or non-homologous chromosome comprises a normal diploid strain containing the following additional chromosome that Is unrelated at the DNA level to any other chromosome In the cell, except for the centromere, the telomeres and the genetic markers.

Figure 5:
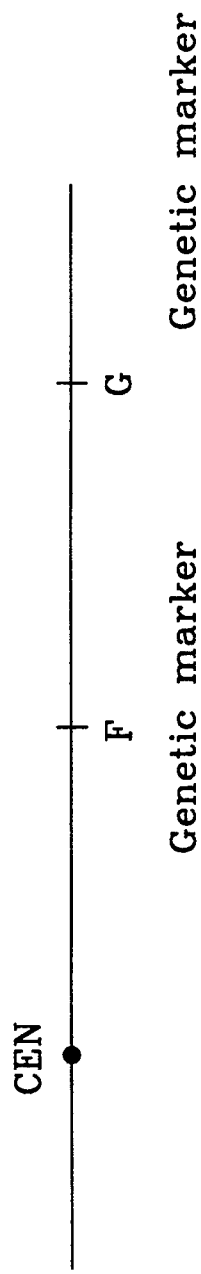
FIG. 5 is an illustration depicting an additional chromosome which can be contained in a normal diploid strain of yeast so that the strain can be used to detect double-stranded DNA damage, where "CEN" denotes the position of the centimeter on the chromosome.

Genetic marker G shown in FIG. 5 identifies the presence of the chromosome. Genetic marker F, also shown in FIG. 5, results in sensitivity to agent K (such as 5-fluoro-orotic acid). The gene F (such as the URA3 gene of yeast) leads to the processing of agent K to a toxic form. Contained In the genome in homozygous condition are mutations of the gene F (i.e., URA3 homozygous mutations). Loss of the nonhomologous artificial chromosome ls further indicated by loss of associated genetic marker G.

A unique feature of the present Invention is that damage can be detected at very low doses of exposure since most damage in the total genome will occur in homologous chromosomes and will therefore be repaired. A double-strand damage event in the divergent chromosomes is not lethal and the efficiency of Induction of genetic change can be as high as 0.3 to 1 per damage event in the divergent chromosomes.

Unless defined otherwise, all technical and scientific terms used herein have the same meaning as commonly understood by one of ordinary skill in the art to which this invention belongs. Although any methods and materials similar or equivalent to those described herein can be used in the practice or testing or the present invention, the preferred methods and materials are now described. All publications mentioned hereunder are incorporated herein by reference. Unless mentioned otherwise, the techniques employed herein are standard methodologies well known to one of ordinary skill In the art.

MATERIALS AND METHODS

The following is an example for the detection system involving nonselective genetic detection.

STRAINS: Strains 230283BI-57 and 021281AI-6 are derived from the Cold Spring Harbor collection (Table 1). The his− alleles in each diploid strain are complementing (i.e., HIS−). Strains 300686C-2, 300686H-45 and 290986C-34a, are S. cerevisiae haploid with chromosome III replaced by a divergent chromosome from S. carlsbergensts. The his4 alleles in the S. carlsbergensis chromosomes were induced by ethyl methane sulronate. The allales belong to the hts4A and the his4C region based on complementation patterns with known S. cerevtstae his4 alleles.

Figure 1:
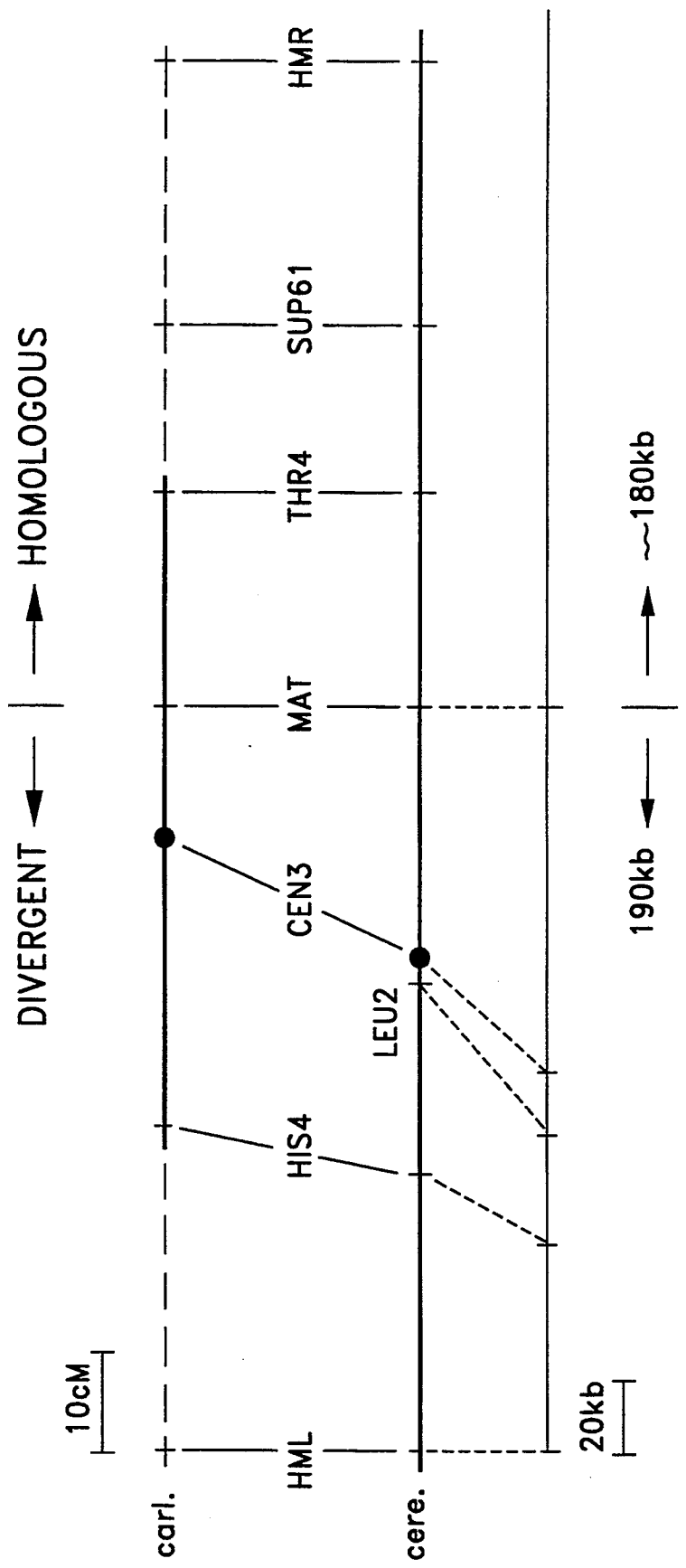
FIG. 1 represents the genetic maps of chromosome III from *S. carlsbergenesis* (carl.) and *S. cerevtstae* (cere.). The lower line corresponds to the physical map of the *S. cerevisiae* chromosome. The dashed line corresponds to an unmapped region.

S. carlsbergensis chromosome III is functionally homologous to chromosome III of S. cerevtslae; however, genetic as well as molecular analyses indicate that the chromosome is composed of two different sections with the left part of FIG. 1 being divergent from and the right part homologous to the S. cerevisiae chromosome (FIG. 1). No meiotic recombination occurs in the region from HML (near the left telomere in FIG. 1) to MAT. This is believed to result from nucleotide sequence differences In this region, as shown for four loci (HML, HIS4, LEU2 and MAT exhibit about 80–90% DNA homology). In the region to the right of MAT, the recombination levels are normal for the MAT-THR4 interval and the molecular structure of SUP61 and HMR appear identical to those of S cerevisiae.

Noncomplementing heteroallelic dtploids carrying one S. carlsbergcrisis allele and one S. cerevisiae allele exhibit spontaneous and ultraviolet light induced mitotic recombination levels that are both 100–1000 fold lower than in similar pure S. cerevtslae strains. Since recombination is greatly reduced, stable dtploids with complementing heteroalleles can be constructed. The appearance of histidine auxotrophs in such diploids with complementing histidine heteroalleles is likely to signal genetic events other than recombination.

GROWTH CONDITIONS AND IRRADIATION: Culture medium and growth procedures employed are standard for yeast genetic analysis. For example, the defined synthetic medium, the canavantne containing medium and the rich nutrient medium (YEPD) are described below. Media designed to test for the absence of a genetic marker contains the components of synthetic complete medium less the nutrient (i.e., amino acid) of interest.

For selective detection systems cells are plated to media that Inhibits growth unless the relevant genetic marker is lost. Media containing 5-Fluoro-orotic acid to select for ura3 auxotrophs has been described in Boeke et al, Molec. Gen. Genet (1984) 197: 345–346. Medium containing canavanine to select for the canavanine resistance (canR) phenotype contains the components of synthetic complete medium less arginine and containing 60 micrograms/ml canavanine.

Cells are grown to stationary phase in YEPD or they can be grown in medium selective for the presence of the pair of homoeologous chromosomes (to eliminate any possible background aneuploldy).

Following exposure to the treatment of Interest. Cells are plated to selective medium If the indicator genetic marker is a selectable marker such as canavanine resistance (canR mutants) or ability to grow on 5-fluoro-orotic acid (ura3 mutants). Alternatively they are plated to nonselective medium (YEPD) if a nonselectable marker system is used.

Aneuploidy, for one of a pair of divergent chromosomes Is determined by examination of colonies for coincident appearance of other genetic markers on the same chromosome. For example, colonies selected on 5-FOA or canavanine would be replicated to appropriate Indicator medium to determine the appearance of other recessive markers on the same chromosome. For the case of a nonselectable system. colonies are replicaplated to appropriate medium to determine the appearance of all the markers for a given chromosome. In the case of the system based on an artificial or nonhomologous chromosome, the loss of the chromosome is substantiated by loss of all the members associated with the chromosome.

A specific example for detecting chromosome 5 aneuploidy, involves the use of a strain that contains one chromosome 5 that is of *Saccharomyces cerevisiae* origin and one that is of *Saccharomyces carlsbergensis* origin such as the *Saccharomyces cerevisiae* strain MR122 (deposited on Mar. 21, 1994 at the American Type Culture Collection, 12301 Parklawn Drive, Rockville, MD 20852, Accession Number 74277). The first chromosome has a ura3 and his1 mutation; the second has a canR and trp2 or 11vl mutation. These mutations are on opposite sides of their respective centromeres. Cells are exposed to low doses. preferably nonlethal doses of an agent. They are plated to 5-FOA and to canavanine containing medium as well as YEPD to determine cell viability. The colonies arising on the 5-FOA or canavanine are tested (either individually or by replica-plating) for the presence of the other chromosomal marker (which is on the opposite side of the centromere). If a nonselective protocol is used, the colonies that arise after cells are plated to YEPD are replica-plated to the appropriate media to determine which (if any colonies) are aneuploid.

Since it is possible to integrate the URA3 gene, the CAN1 gene as well as other resistance/sensitive genetic systems into any chromosome of yeast using standard molecular biology techniques, the system of the present Invention can be employed for any desired chromosome.

| SYNTHETIC COMPLETE MEDIUM | |
|---|---|
| DEXTROSE | 20 GM/L |
| BACTO-YEAST NITROGEN BASE (w/o AMINO ACIDS OR AMMONIUM SULFATE) | 1.7 GM/L |
| AMMONIUM SULFATE | 5.0 GM/L |
| L-ADENINE SULFATE | 10 µg/ml |
| L-ARGININE.HCl | 50 µg/ml |
| L-ASPARTIC ACID | 25 µg/ml |
| L-HISTIDINE.HCl | 20 µg/ml |
| L-GLUTAMIC ACID | 100 µg/ml |
| L-ISOLEUCINE | 50 µg/ml |
| L-LEUCINE | 100 µg/ml |
| L-LYSINE.HO1 | 50 µg/ml |
| L-METHIONINE | 20 µg/ml |
| L-PHENYLALANINE | 50 µg/ml |
| L-SERINE | 375 µg/ml |
| L-THREONINE | 100 µg/ml |
| L-TRYPTOPHAN | 50 µg/ml |
| L-TYROSINE | 50 µg/ml |
| URACIL | 20 µg/ml |
| L-VALINE | 150 µg/ml |
| Adjust pH to 5.8 with NaOH or HCl. Then add 20 GM PHYTAGAR per liter. Dissolve, mix, dispense, autoclave 25 minutes. Pour plates with 30–35 ML/PLAT | |
| YEPD | |
| DEXTROSE | 20 GMs |
| BACTO-PEPTONE | 20 GMs |
| BACTO-YEAST EXTRACT | 10 GMs |
| BACTO-AGAR | 20 GMs |
| DEIONIZED H$_2$O | 1000 MLs |
| Dissolve, mix, autoclave 30 mins. After autoclaving, before pouring, cool medium in constant temperature water bath to 60° C. Using sterile technique, add the following sterile solution: | |
| TETRACYCLINE - HCl (2 mg/ml) | 10 ML |
| ADENINE 0.5% SOLUTION | 2 ML |
| or | |
| ADENINE 2 mg/ml | 5 ML |
| Mix well, dispense 30–35 ML into sterile Petri dishes. | |

For an example of a nonselective system based on complementing HIS4 alleles in a pair of divergent chromosomes (chromosome III), cells were grown in histidineless medium for two to three days. Since approximately 95% of the cells lacked buds, only 5were in the S or G-2 phase of the cell cycle. Cells were washed with water, resuspended at $5 \times 10^4$ cells per ml and irradiated at 0° C. In a Shepherd Mark I, ≃Cesium Irradiator, Model 68-A, at a dose rate of 3.6 krad/mtn. Cells were diluted and plated to YEPD and grown at 30° C. Colonies were replicated to the appropriate media to determine genotype and aneuploidy.

GENETIC ANALYSIS: To establish the induction of aneuploidy standard tetrad analysis methods were used. To investigate whether strains expressing the MATa or MATα mating type were monosome or euploid for chromosome III, they were crossed to appropriately marked diploids. For isolates expressing the *S. carlsbergensis* specific markers (his4-S3 and MATα) the tester strain was a diploid monosomic for chromosome III (hts4-15 leu2 MATa thr4). For isolates expressing the *S. cerevisiae* specific markers (hls4-15 leu2 MATa and thr4) the tester strain carried two copies of the *S. carlsbergensis* chromosomes III (hls4-3 MATα). The resulting tetraploids were sporulated and dissected. Based on the mating characteristics of spore colonies from the tetrads and the segregation of the his4 and leu2 markers, it was possible to assess If the original diploids were monosome or euploid. Because homologous chromosomes (*cerevisiae* or *carlsbergensis*) preferentially disjoin in melosis and there is no recombination between the linked genes HIS4, LEU2 and MAT, this linkage group segregates in the first melotic division.

PHYSICAL ANALYSIS OF CHROMOSOMES: To analyze the chromosomes, chromosomes were separated according to size using pulse field gel electrophoresis methods (OFAGE).

RESULTS

RADIATION-INDUCED LOSS OF GENETIC MARKERS IN DIVERGENT VS HOMOLOGOUS PAIRS OF CHROMOSOME III USING A NONSELECTABLE GENETIC SYSTEM: In yeast the repair of radiation-induced DSBs, as well as other double-strand damage involves recombination and a reduction in homology is expected to reduce repair. To examine the consequences of reducing the opportunity for recombination, we developed diploid strains in which all but one (Chromosome III) of the sixteen pairs of chromosomes are homologous. The remaining pair is divergent (i.e., homoeologous); one chromosome is derived from *S. carlsbergensis* and the other from *S. cerevisiae*. Nearly half of the chromosome III pair exhibits no or greatly reduced recombination in both meiosis and mitosis (from MAT to the left telomere); a high level of DNA homology exists in the other half (FIG. 1). The system which was developed to detect possible damage-induced genetic changes was based on complementing mutations in the HIS4 locus at different functional regions of the locus. Loss of an allele results in histidine auxotrophy and can be detected by replicaplating colonies that arise on rich medium to histidineless medium. At high levels of survival. This also allows sectored rs. whole colony events to be discriminated.

Figure 3:
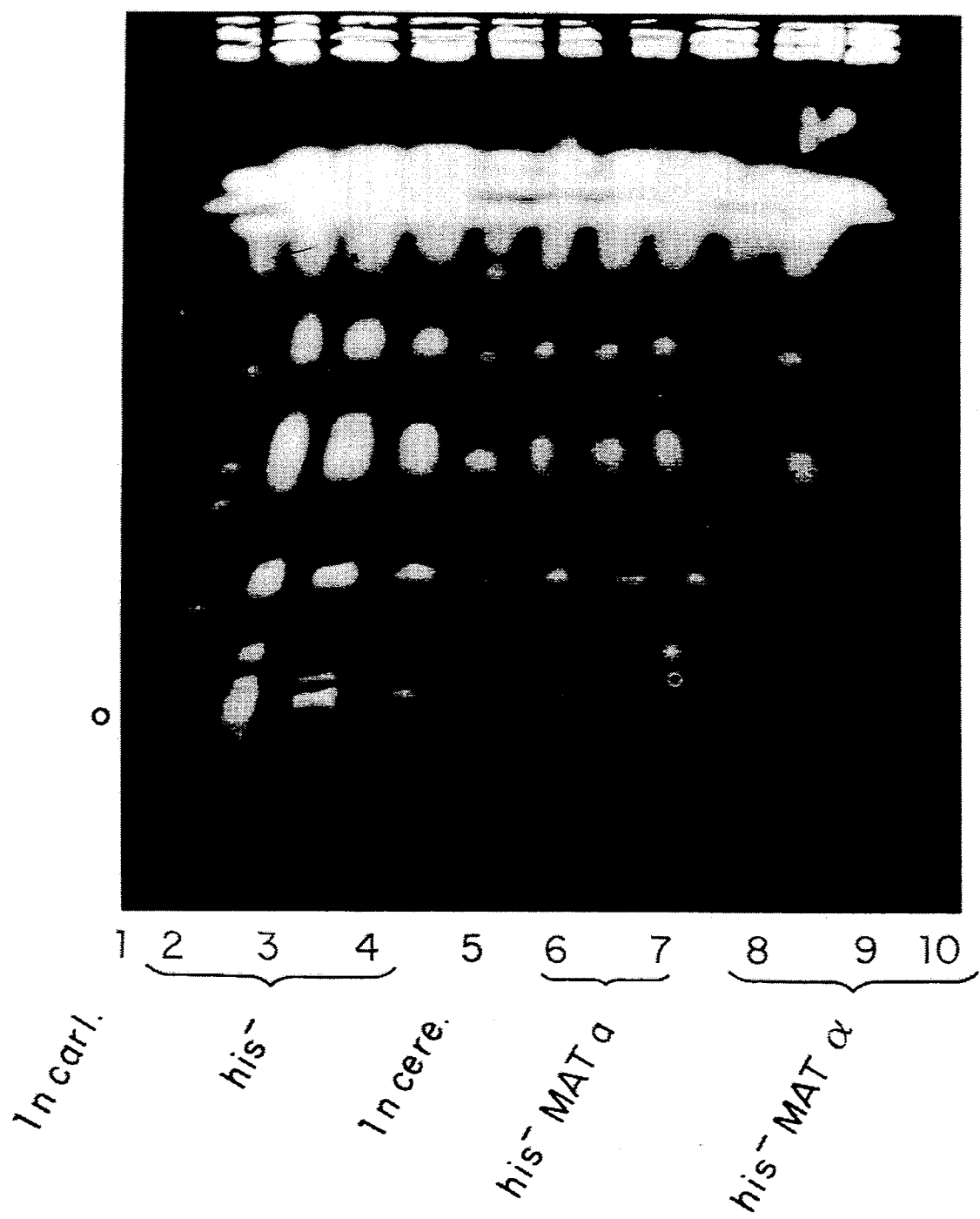
FIG. 3 shows the OFAGE analysis of chromosomal DNA extracted from his⁻ haploid parents and radiation-induced his⁻ isolates of strain D-VG (deposited on Mar. 21, 1994 at the American Type Culture Collection, 12301 Parklawn Drive, Rockville, MD 20852, Accession Number 74276). This strain is a *Saccharomyces cerevisiae* strain which contains one *Saccharomyces cerevisiae* chromosome III and one *Saccharomyces carlsbergensis* chromosome III (see Table 1). Lane 1, haploid parent 300686C-2 (carlsbergen.Sis); lane 5, haploid parent 021281AI-6 (cerevlslae); lanes 2, 8, and 4 correspond to his⁻ (only) Isolates from strain D-VG; lanes 6 and 7, his⁻ leu⁻ MATa thr⁻ isolates of strain D-VG; lanes 8, 9, 10, his⁻ MATα isolates of strain D-VG. The chromosomes III of the diploid parent D-VG migrate as expected based on the haploid parents (data not shown).

Exposure of the divergent chromosome III strain to nonlethal doses of radiation induced high frequencies of his⁻ colonies. After only 5 krad, the histidine auxotroph frequency was approximately 3%, and this increased linearly to approximately 20 krad (Table 2). The induction of his⁻ colonies was much lower in homologous strains. Over 95% of the his⁻ colonies derived from the divergent strain also expressed a mating type allele. Nearly half were MATa and expressed leu2 and thr4; the other half expressed MATα. Since HIS4 and MAT are located on either side of the centromere, the radiation efficiently induced aneuploidy and/or malsegregation of the S. carlsbergensis chromosome. As mentioned below, the events are primarily due to chromosome loss. The lack of genetic markers on the S. carlsbergensis chromosome might render analysis of remaining his⁻ colonies somewhat less accurate. However, the comparable frequency of his⁻ MATα and his⁻ leu⁻ MATα thr⁻ colonies (Table 2) indicates that events involving the S. cerevisiae chromosome occur with similar frequency (even when there is an additional copy of the S. carlsbergensis chromosome; see D-VGG in Table 2 and FIG. 3).

It was, therefore, concluded that low doses of ionizing radiation (FIG. 2B) can be efficient inducers of chromosome loss. Few, if any, events could be explained by multiple reciprocal recombination events since the frequency of the his⁻ only category (histidine auxotrophs not expressing mating type) is low (Table 3). Furthermore, the cells were predominantly (>95%) in the G-1 phase of the cell cycle when irradiated which would preclude the detection of reciprocal exchange events.

Figure 2A:
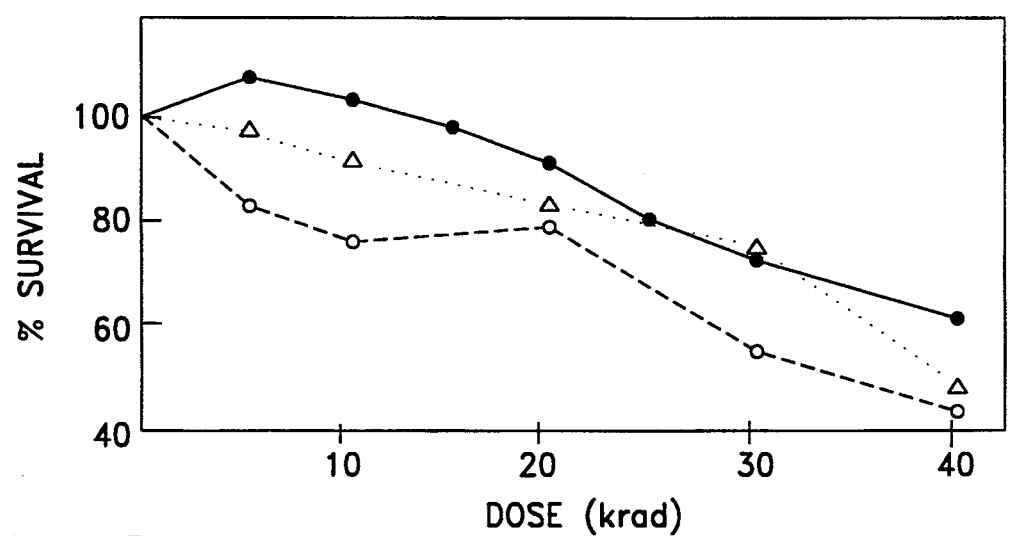
FIGS. 2A and 2B show the results of induction, by ionizing radiation, of chromosome III aneuploidy in strains that are DNA divergent (—), homologous *S. cerevisiae* (—), or homologous *S. carlsbergensis* (—) for chromosome III. Also included are results with a trisomic chromosome III strain that has two copies of the *S. carlsbergensis* chromosome III and one copy of the *S. cerevisiae* III (. . . . .). Presented is total aneuploidy for chromosome III based on the data in Table I. The two results for the divergent experiment are averaged; the results for the homologous experiments are pooled between experiments (because of the small number of events). Also shown (—) is the expected induction of DSBs as a function of dose in a 360 kb stretch of DNA(180kb x 2); this corresponds to the divergent portion of the chromosomes.
Figure 2B:
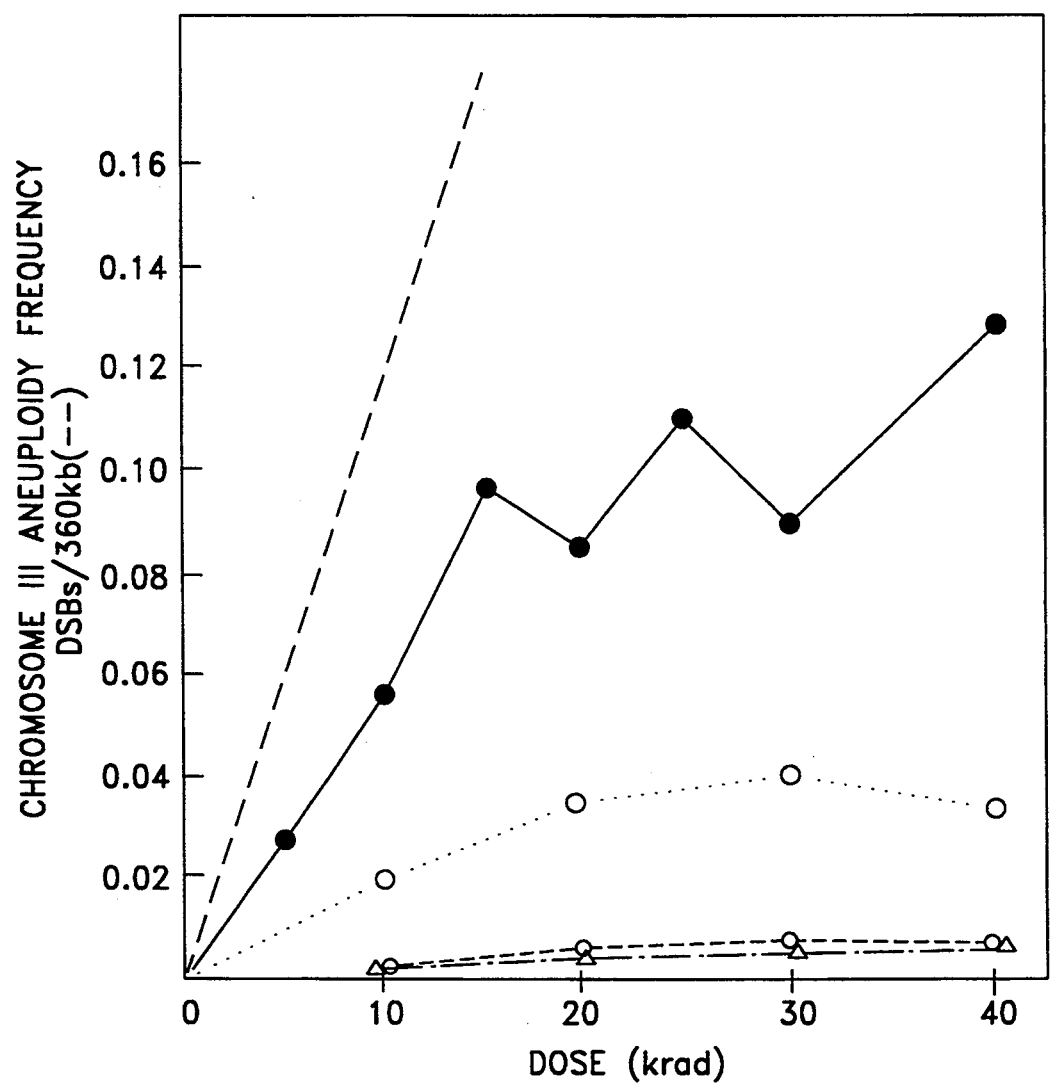

The chromosome III loss frequency in the homologous strains was 20 to 50 fold lower than for the divergent strains (FIG. 2B and Table 2). Based on the data in Tables 2 and 3, the low level of MATa or MATα histidine auxotrophs found in the homologous chromosome experiments cannot be explained by recombination on both sides of the centromere. Thus, precise homology greatly reduces the potential for radiation-induced chromosome loss.

MECHANISM OF CHROMOSOME LOSS: The above results could also have arisen by nondisjunction of a sister chromatid pair resulting in a monosomic and a trisomic daughter cell, nondisjunction of pairs of sister chromatids resulting in two daughter cells both euploid for chromosomes III, or by chromosome loss so that the progeny would only be monosomic. If the first hypothesis were true, the colonies containing his⁻ cells should be sectored (his⁻/HIS+). If the second hypothesis were true, the colonies would be entirely his⁻ but they would be sectored for the associated mutations on chromosome III. The results indicate that only 5% of his⁻ colonies showed evidence of his⁻/HIS+ sectors; the rest were whole his⁻ colonies. The lack of sectoring is not due to a growth advantage by either his⁻ or HIS+ cells nor lethal sectoring since non-lethal doses were used. It was, therefore, concluded that the radiation-induced appearance of his⁻ colonies in the divergent strain is largely the result of chromosome loss in the G-1 cells.

Chromosome loss was examined further genetically and by karyotype analysis using OFAGE methods to display chromosomes (Carle et al, 1985, Proc. Natl. Acad. Sot. USA 82, 3756-3760). Eleven his⁻ leu⁻ MATa thr⁻ strains were crossed with a diploid that was carrying two copies of the S. carlsbergensis chromosome III found in strain 300686C-2. Following meiosis, the tetrads contained two his⁻ MATα cells and two HIS+ nonmaters (hls4-15 and hts4-S3 are complementing). Since all the cells were also LEU+ and THR+, the tested strains were monosomic for chromosome III, presumably from S. cerevlsiae. This was confirmed using OFAGE analysis (lanes 6 and 7 in FIG. 3; the Intensity of the chromosome III was approximately half that of the chromosome VI band). Thus when the S. cerevisiae chromosome is retained, the radiation-induced loss of a divergent chromosome results in monosomy.

When the S. carlsbergensis chromosome III is retained. the situation is somewhat different. Nine his⁻ Leu + MATα THR+ isolates were tested genetically by crossing to a diploid monosomic for a his⁻ S. cerevisiae chromosome III. Four produced tetrads containing only his⁻ spores of either MATa or MATα mating types and were monosomic for chromosome III. The remaining five strains were euploid for chromosome III since they yielded tetrads in which HIS+/his⁻ segregated 2:2 and the HIS+ strains were nonmaters. OFAGE analysis confirmed euplotdy for three strains (lanes 8, 9, and 10) in FIG. 3. The intensity of the S. carlsbergensis chromosome III band approximately equals the intensity of the chromosome VI band (migrating slightly faster than chromosome III). It is possible that euplotdy results as a consequence of a secondary event following loss of the S. cerevisiae chromosome and is selected during clonal outgrowth.

INDUCTION OF OTHER GENETIC EVENTS: Among the his⁻ colonies arising from the divergent strains after low doses, nearly all were associated with the appearance of other genetic markers (Table 3). Of 358 his⁻ colonies recovered from all doses in two experiments, all but twenty could be attributed to chromosome loss. Seven of the twenty were his⁻ and five of these were examined with the OFAGE system. Three appeared to contain a S. cerevisiae chromosome III with reduced mobility (one of these corresponds to lane 3 in FIG. 3). The other two did not exhibit chromosome rearrangements (lanes 2 and 4 in FIG. 3). The origin of the genetic change in these cells remains unknown; however, it is possible that a rare gene conversion may have occurred even though there is limited homology. Among the remaining 13 colonies, 7 could be explained by chromosome loss and associated recombination between MAT and THR4. One colony appears to have resulted from a break or recombinational event between LEU2 and the centromere. The other 5 colonies remain unexplained.

While the total frequency of his⁻ colonies was much lower In the homologous strains, the frequency of the "his⁻ only" category among these colonies was much higher, presumably, due to recombination. Somewhat comparable numbers of colonies that were only thr⁻ occurred with both types of strains; they probably arose by recombination between the MAT and THR4 loci.

Events on other chromosomes were similar between the various strains. (ade⁻, Table 3; ura⁻, data not presented). Comparable levels of homozygosis would be expected to occur by recombinational repair between homologous chromosomes.

The yeast based genetic system of the present invention allows rapid assessment of the effect of any chemical or physical agent in causing double-strand DNA damage either directly or as a consequence of processing of the DNA lesions (as might occur during repair). The absence of homology in G-1 cells, and thus the opportunity for recombinational repair (of DNA double-strand breaks or damage) in the divergent chromosome, results in high levels (about 5 to 10%) of aneuploidy for chromosome III at doses of radiation resulting in almost no killing.

As shown herein, the method for detecting the effect of an agent on chromosomal changes comprises the steps of:

(a) exposing the yeast strain of the present invention to an agent whose DNA damaging effect is to be determined;

(b) then plating the strain from step (a) to a suitable selective or diagnostic medium; and (c) thereafter examining plated colonies of step (b) for the loss of a DNA divergent homoeologous chromosome from a pair of divergent chromosomes or loss of a nonhomologous or artificial chromosome.

It is understood that the examples and embodiments described herein are for illustrative purposes only and that various modifications or changes in light thereof will be suggested to persons skilled In the art and are to be included within the spirit and purview of this application and scope of the appended claims.

TABLE 1

Genotypes of strains

| Strain | Chromosome | | | Genotype | | | | |
|---|---|---|---|---|---|---|---|---|
| D-VG | (cerevisiae) 021281AI-6 | his4-15 | leu2 | MATa | thr4 | ade2 | + | cyh2 |
| | 300686C-2 (carlsberg) | his4-S3 | + | MATα | + | + | ade1 | + |
| | | + | ura3 | + | + | | | |
| | | can1 | + | lys2 | ura4 | | | |

D-VGG Same as D-VG except the strain is disomic for the S. carlsberg chromosome.

| H-VV | 021281AI-6 | his4-15 | leu2 | MATa | thr4 | ade2 | cyh2 | ura3 | + |
|---|---|---|---|---|---|---|---|---|---|
| | 230283BI-57 (cerevisiae) | his4-290 | + | MATα | + | + | + | + | lys1 |

| H-GG | (carlsberg) 300686H-45 | his4-S7 | + | MATa | ade1 | lys2 | can1 | + |
|---|---|---|---|---|---|---|---|---|
| | 290986C-34a (carlsberg) | his4-S3 | + | MATα | + | + | + | ura3 |

TABLE 2

The induction of aneuploidy in strains that are divergent (D-VG) or homologous (cerevisiae, H-VV, or carlsbergensis, H-GG) for chromosome III

| Homologous (H) or Divergent (D) Strain | Dose (krad) | Total Colonies | % his⁻* | % chromosome lost** | |
|---|---|---|---|---|---|
| | | | | α | a |
| H-VV | 0 | 842$^a$ | <0.1 | 0 | 0 |
| H-VV | 0 | 1370$^b$ | <0.1 | 0 | 0 |
| H-GG | 0 | 1213$^a$ | <0.1 | 0 | 0 |
| D-VG | 0 | 454$^a$ | <0.2 | 0 | 0 |
| | 0 | 1088$^b$ | <0.1 | 0 | 0 |
| D-VGG*** | 0 | 1118 | <0.1 | 0 | 0 |
| D-VG | 5 | 303$^a$ | 2.7 | 1.7 | 1.0 |
| D-VG | 5 | 382$^b$ | 3.5 | 1.1 | 2.4 |
| H-VV | 10 | 414$^a$ | 0.5 | 0 | 0.2 |
| H-VV | 10 | 1620$^b$ | 0.2 | 0 | 0.06 |
| H-GG | 10 | 1168 | 0.4 | 0 | 0 |
| D-VG | 10 | 321$^a$ | 5.6 | 3.4 | 2.2 |
| D-VG | 10 | 650$^b$ | 5.4 | 2.5 | 2.8 |
| D-VGG*** | 10 | 688 | 2.0 | 0 | 1.9 |
| D-VG | 15 | 424$^b$ | 10.6 | 3.3 | 6.4 |
| H-VV | 20 | 429$^a$ | 0.7 | 0.2 | 0.2 |
| H-VV | 20 | 2785$^b$ | 1.1 | 0.18 | 0.29 |
| H-GG | 20 | 2597 | 1.0 | 0.19 | 0.16 |
| D-VG | 20 | 274$^a$ | 9.9 | 6.6 | 2.9 |
| D-VG | 20 | 390$^b$ | 8.0 | 2.1 | 5.4 |
| D-VGG*** | 20 | 382 | 3.7 | 0 | 3.4 |

TABLE 2-continued

The induction of aneuploidy in strains that are divergent (D-VG) or homologous (cerevisiae, H-VV, or carlsbergensis, H-GG) for chromosome III

| Homologous (H) or Divergent (D) Strain | Dose (krad) | Total Colonies | % his⁻* | % chromosome lost** | |
|---|---|---|---|---|---|
| | | | | α | a |
| D-VG | 25 | 244$^b$ | 11.1 | 7.0 | 4.1 |
| H-VV | 30 | 373$^a$ | 1.1 | 0.3 | 0.6 |
| H-VV | 30 | 1047$^b$ | 1.2 | 0.1 | 0.6 |
| H-GG | 30 | 1284 | 1.6 | 0.16 | 0.4 |
| D-VG | 30 | 328$^a$ | 12.5 | 6.1 | 5.5 |
| D-VG | 30 | 397$^b$ | 7.8 | 3.5 | 2.8 |
| D-VGG*** | 30 | 382 | | | (4.0) |
| H-VV | 40 | 287$^a$ | 0 | 0 | 0 |
| H-VV | 40 | 1184$^b$ | 1.6 | 0.17 | 0.68 |
| H-GG | 40 | 1148 | 1.4 | 0.26 | 0.43 |
| D-VG | 40 | 309 | 12.3 | 6.1 | 5.8 |
| D-VG | 40 | 252 | 15.5 | 7.5 | 6.4 |
| D-VGG*** | 40 | 380 | | | (3.4) |

*Frequency of total colonies that require histidine for growth. In the controls (0 krad) no his⁻ colonies were detected.
**Frequency of total colonies that are due to loss of the S. carlsbergenis chromosome III and are, therefore, his⁻ leu⁻ MATa thr⁻ or due to loss of the S. cerevisiae chromosome III and are, therefore, his⁻ MATα.
***This is a strain that is disomic for the S. carlsbergenis chromosome III. The results in parentheses correspond to the total frequency of his⁻ colonies. Based on results with 10 and 20 krad, most of these are likely to be due to loss of the S. cerevisiae chromosome.
"a" or "b" indicates two experiments done on different days.

TABLE 3

Expression of recessive markers in colonies from irrradiated* (10 & 20 krad) cells of divergent (D-VG) or homologous (H-VV or H-VG) strains

| Strains | Dose (krad) | Colonies examined | % his⁻ only | % thr⁻ only | % ade⁻ only |
|---|---|---|---|---|---|
| D-VG | 10 | 971 | 0.1 (1)** | 0.2 (2) | 2.2 |
| D-VG | 20 | 664 | 0.2 (1) | 0.8 (5) | 4.3 |
| H-VV | 10 | 2034 | 0.1 (2) | 0.2 (4) | 2.1 |
| H-VV | 20 | 3214 | 0.6 (18) | 0.2 (7) | 3.8 |
| H-GG | 10 | 1168 | 0.4 (5) | — | 1.2 |
| H-GG | 20 | 2597 | 0.6 (16) | — | 1.4 |

*Among the colonies arising from unirradiated cells (see Table 2), none expressed the recessive markers described in this table.
**Corresponds to the number of colonies. The ada⁻ colonies were observed from a much larger sample and therefore the numbers of colonies are not presented. The divergent strain is +/ade1 +/ade2; the H-VV strain is +/ade2 and the H-GG strain is +/ade1. The distances to the centromere of the ADE2 and ADE1 genes are approximately 65 cM and 5 cM, respectively, which accounts for the differences in response between the H-VV and H-GG strains.

What is claimed is:

1. A method for determining the ability of an agent to produce chromosome loss comprising:

administering an agent to diploid *Saccharomyces cerevisiae* cells, wherein each of said cells comprise at least one homoeologous chromosome pair, said pair consisting of a first and a second chromosome, said first chromosome comprising a DNA sequence which is sufficiently different from the DNA sequence of said second chromosome such that homologous recombination of said first and second chromosomes is prevented, each of said first and second chromosomes comprising a phenotypic marker which is distinguishable from any other marker in each of said cells;

plating said cells on a medium suitable for selecting said markers or diagnosing the presence of said markers; and examining the phenotypes expressed by said cells to determine whether the loss of one of said chromosome pair has occurred in those cells.

2. A method of claim 1, wherein said first chromosome is a *Saccharomyces cerevisiae* chromosome 3 and said second chromosome is a *Saccharomyces carlsbergensis* chromosome 3.

3. The method of claim 1, further comprising the step of replica-plating the cells plated on said medium onto a second selective or diagnostic medium.

4. The method of claim 1, wherein said first chromosome is a *Saccharomyces cerevisiae* chromosome 5 and said second chromosome is a *Saccharomyces carlsbergensis* chromosome 5.

* * * * *